(12) United States Patent
Finger et al.

(10) Patent No.: US 9,165,692 B2
(45) Date of Patent: Oct. 20, 2015

(54) RADIOACTIVE GLASS SOURCE

(71) Applicant: IP LIBERTY VISION CORPORATION, New York, NY (US)

(72) Inventors: Paul T. Finger, New York, NY (US); Toby Welles, Redding, CT (US)

(73) Assignee: IP LIBERTY VISION CORPORATION, New York, NY (US)

( * ) Notice: Subject to any disclaimer, the term of this patent is extended or adjusted under 35 U.S.C. 154(b) by 0 days.

(21) Appl. No.: 14/243,683

(22) Filed: Apr. 2, 2014

(65) Prior Publication Data

US 2015/0102238 A1    Apr. 16, 2015

Related U.S. Application Data

(60) Provisional application No. 61/891,351, filed on Oct. 15, 2013.

(51) Int. Cl.
| | |
|---|---|
| G21H 1/00 | (2006.01) |
| G21H 3/00 | (2006.01) |
| G21H 5/00 | (2006.01) |
| G21G 4/06 | (2006.01) |
| G21G 4/00 | (2006.01) |
| A61N 5/10 | (2006.01) |
| G21G 4/08 | (2006.01) |
| G21F 3/00 | (2006.01) |
| G21F 5/015 | (2006.01) |

(52) U.S. Cl.
CPC .. *G21G 4/06* (2013.01); *A61N 5/10* (2013.01); *G21G 4/00* (2013.01); *G21G 4/08* (2013.01); *G21F 3/00* (2013.01); *G21F 5/015* (2013.01)

(58) Field of Classification Search
CPC ...... G01T 1/1644; G01T 1/2018; G01T 1/202
USPC ............... 250/339.06, 493.1, 503.1, 505.1
See application file for complete search history.

(56) References Cited

U.S. PATENT DOCUMENTS

| | | | |
|---|---|---|---|
| 2,517,553 A | 8/1950 | Hissong | |
| 2,559,393 A | 7/1951 | Pregel | |
| 4,362,659 A | 12/1982 | Macedo et al. | |
| 4,607,164 A * | 8/1986 | Kubota et al. | 250/363.02 |
| 5,011,677 A | 4/1991 | Day et al. | |
| 5,302,369 A | 4/1994 | Day et al. | |
| 5,977,556 A * | 11/1999 | Qiu et al. | 250/585 |
| 6,666,811 B1 | 12/2003 | Good | |
| 6,689,043 B1 | 2/2004 | McIntire et al. | |
| 6,986,880 B2 | 1/2006 | Coniglione et al. | |
| 7,453,984 B2 | 11/2008 | Chen et al. | |

(Continued)

FOREIGN PATENT DOCUMENTS

EP    1 873 788 A1    1/2008

OTHER PUBLICATIONS

International Search Report for PCT Application No. PCT/US14/60203 mailed on Jan. 2, 2015.

*Primary Examiner* — Nikita Wells
(74) *Attorney, Agent, or Firm* — Pearl Cohen Zedek Latzer Baratz LLP; Mark S. Cohen

(57) ABSTRACT

A glass radiation-source with customized geometries to maximize receipt of radiation into treatment areas that is formed from either neutron-activated glass, radioisotopes molecularly bonded to glass, or radioisotopes encased within glass.

17 Claims, 5 Drawing Sheets

(56) References Cited

U.S. PATENT DOCUMENTS

| | | |
|---|---|---|
| 7,792,249 B2 | 9/2010 | Gertner et al. |
| 7,959,900 B2 | 6/2011 | Peng et al. |
| 2011/0201866 A1 | 8/2011 | Cipriani et al. |

* cited by examiner

RADIOACTIVE GLASS SOURCE

CROSS REFERENCE TO RELATED APPLICATIONS

This application claims the benefit of U.S. Ser. No. 61/891,351, filed on Oct. 15, 2013, which is incorporated by reference herein in its entirety.

FIELD AND BACKGROUND OF THE INVENTION

The present invention generally relates to brachytherapy, and specifically, relates to glass radiation-sources with customized geometries to maximize receipt of radiation into treatment volumes of various sizes, surface geometries, and shapes.

BRIEF DESCRIPTION OF THE DRAWINGS

The subject matter regarded as the invention is particularly pointed out and distinctly claimed in the concluding portion of the specification. The invention, in regards to its features, components and their configuration, operation, and advantages are best understood with reference to the following description and accompanying drawings in which:

Figure 1:
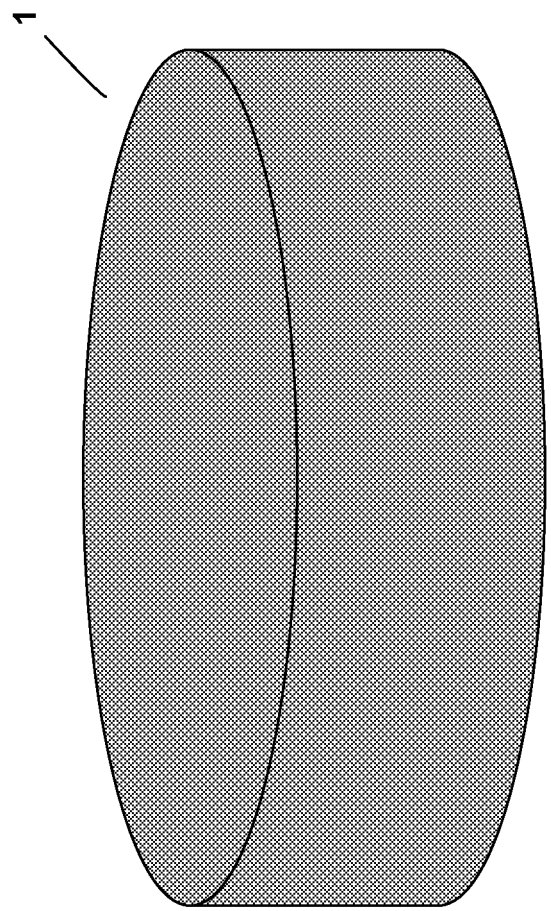
FIG. 1 is a schematic, perspective view of a neutron-activated glass disk, according to an embodiment.

It will be appreciated that for clarity elements shown in the figures may not be drawn to scale. Furthermore, reference numerals may be repeated among the figures to indicate corresponding or analogous elements where deemed appropriate.

DETAILED DESCRIPTION OF EMBODIMENTS OF THE PRESENT INVENTION

In the following detailed description, numerous details are set forth in order to provide a thorough understanding of the invention. However, it will be understood by those skilled in the art that the present invention may be practiced without these specific details and that well-known methods, procedures, and components have not been described in detail so as not to obscure the present invention.

Embodiments of the present invention are generally directed to custom formed glass, radiation-source The following terms will be used out through the document:

"Radiation-source", "source", "source material", "radioactive-source", "radioisotope" all refer to a radioactive material emitting therapeutic or non-therapeutic radiation.

"Proximity" or "close proximity" refer to a distance between a radiation-source and a surface of a treatment volume in which a therapeutic or otherwise beneficial dose of radiation radiates.

"Surface geometry" refers to the angularity of the surface.

"Shape" refers to the contour or the outer boundary of an object.

"Treatment area" refers to either a biological or a non-biological area to which the radiation is targeted. The treatment area is typically the interface between the glass, radiation-source and the treatment volume.

"Particulate radioisotopes" include particulate radioisotopes either encased or held within either a primary or a secondary matrix or a combination of both.

Turning now to the figures, FIG. 1 depicts a generally cylindrical, glass radiation-source 1 or disk having a thickness of approximately 1.0 mm thick and diameter between about 2.0 mm to 22.0 mm. It should be appreciated that glass radiation source 1 can be formed into symmetrical or asymmetrical shapes of assorted surface geometries so as to modulate the radiation field in accordance with a particular need. Without diminishing in scope, a disk-shaped radiation source will be discussed in this document.

In certain embodiments, glass radiation-source 1 contains radioisotopes that emit any one or a combination of alpha particles, beta minus and beta plus particles, positrons, Auger electrons, gamma-rays, or x-rays. The choice of radioisotope is determined by the particular therapeutic requirements. In certain embodiments, the radioisotopes are activated through bombardment in a cyclotron with high-energy particles, like neutrons for example. Such materials include, inter alia, yttrium aluminosilicate, magnesium aluminosilicate, holmium-166, erbium-169, dysprosium-165, rhenium-186, rhenium-188, yttrium-90, or other elements on the periodic table.

In certain embodiments, non-radioactive glass is mixed with a radioactive material so as to form a glass-based radioactive mixture. Examples of radioactive materials that may be mixed together with the glass include, inter alia, iodine-125, palladium-103, and strontium-90 to emit low energy gamma rays.

In certain embodiments, glass radiation-source is implemented as glass-encased Auger emitters like, inter alia, 67Ga, 99mTc, 111In, 123I, 125I, and 201Tl.

In certain other embodiments, glass radiation-source is implemented as glass-encased alpha-emitters like, inter alia, uranium, thorium, actinium, and radium, and the transuranic elements.

During manufacture, image data of a treatment area is derived from data provided by three dimensional medical imaging techniques like, inter alia Magnetic Resonance Imaging (MRI), Three-Dimensional Ultrasound, Computed Axial Tomography (CAT or CT), Single-Photon Emission Computed Tomography (SPECT) or Positron Emission Tomography (PET), for example.

The image includes both surface geometry and shape data that can be used in a variety of manufacturing processes like, inter alia cutting, three-dimensional printing, or other rapid prototyping techniques like laser sintering, stereolithography, or fused filament fabrication. It should be appreciated that in a certain embodiment, these processes may be used to produce a mold for casting or forming of the glass radiation source $4b$.

Figure 4:
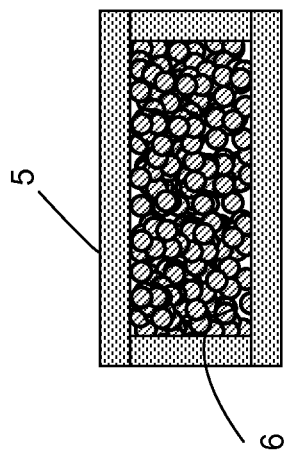
FIG. 4 is a schematic, cross-sectional view of the glass disk of FIG. 2 depicting neutron-activated, glass microspheres encased in a glass encasement, according to an embodiment.
Figure 5:
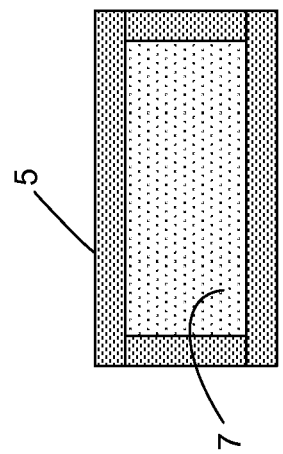
FIG. 5 is a schematic, cross-sectional view of the glass disk of FIG. 2 depicting particulate radioisotope encased in a glass encasement, according to an embodiment.
Figure 2:
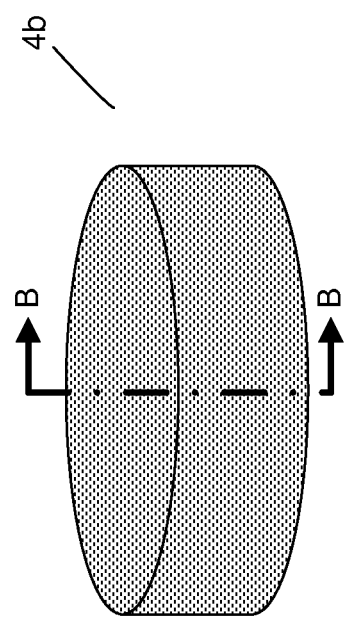
FIG. 2 is a schematic, perspective view of a radioactive, glass disk implemented as a radioisotope encased in a glass encasement, according to an embodiment.
Figure 3:
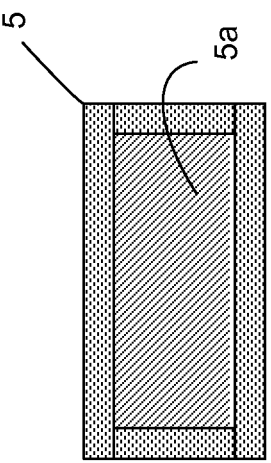
FIG. 3 is a schematic, cross-sectional view of the radioactive glass disk of FIG. 2 depicting a radioisotope encased in a glass encasement, according to an embodiment.

FIG. 2 depicts glass radiation-source $4b$ implemented as a radioisotope encased in a glass encasement. FIGS. 3-5 depict cross-section views along line B-B of embodiments of glass radiation-source $4b$.

FIG. 3 depicts an embodiment of radioisotope $5a$ encased inside glass encasement 5. Radioisotope $5a$ may be selected from any one or a combination of, inter alia, $^{89}Sr$, $^{90}Sr$, $^{169}Yb$, $^{32}P$, $^{33}P$, $^{90}Y$, $^{192}Ir$, $^{25}I$, $^{131}I$, $^{103}Pd$, $^{177}Lu$, $^{149}Pm$, $^{140}La$, $^{153}Sm$, $^{186}Re$, $^{188}Re$, $^{166}Ho$, $^{166}Dy$, $^{137}Cs$, $^{57}Co$, $^{169}Er$, $^{165}Dy$, $^{97}Ru$, $^{193m}Pt$, $^{195m}Pt$, $^{105}Rh$, $^{68}Ni$, $^{67}Cu$, $^{64}Cu$, $^{109}Cd$, $^{111}Ag$, $^{198}Au$, $^{201}Tl$, $^{175}Yb$, $^{47}Sc$, $^{159}Gd$, $^{212}Bi$, and $^{77}As$.

Glass encasement 5 is constructed from silica in certain embodiments; however, it should be appreciated that the glass encasement may be formed from any one or the combination of glass forming oxides including, inter alia Aluminum Oxide, Boric Oxide, Barium Oxide, Calcium Oxide, Potassium Oxide, Lithium Oxide, Magnesium Oxide, Sodium Oxide, Lead Oxide, Tin Oxide, Strontium Oxide, Zinc Oxide, Titanium Dioxide, and Zirconium Oxide.

In certain embodiments, encasement may be constructed from a radiation-permeable coating of metallic or polymeric material to advantageously contain ablation, fragmentation, detachment, degradation, and selective attenuation of radiation emission.

Glass encasement 5 is formed by any one or a combination of manufacturing processes including, inter alia, lamination, casting, drawing, forming, molding, blowing, adhesion, or extrusion.

FIG. 4 depicts an embodiment of radioactive radiation source $4b$ of FIG. 2 in which radioactive microspheres 6 of neutron-activated glass are encased in glass encasement 5.

Radioactive microspheres 6 are implemented from the materials noted above, according to embodiments.

FIG. 5 depicts an embodiment of radioactive radiation source $4b$ of FIG. 2 in which radioisotope is implemented in particulate form having an average diameter ranging between about 0.2-10.0 microns.

Applications of embodiments of customized, glass radiation source include, inter alia, determining the resolving time of Geiger meter counters, nuclear science instruction with experiments involving radioactivity and gamma spectroscopy, and close-proximity radiation therapy as will now be discussed.

Figure 6:
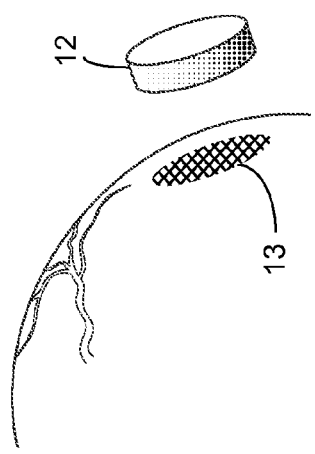
FIG. 6 is a schematic view of a glass, radiation-source having a symmetrical surface geometry substantially corresponding to that of a treatment area, according to an embodiment.

FIG. 6 depicts a custom-formed, glass, radiation-source 12 having a circular shaped face with a flat surface geometry substantially corresponding to the surface area of treatment area 13, according to an embodiment. In brachytherapy, glass, radiation-source 12 is brought into proximity to diseased tissue 13 usually temporarily, as is known in the art.

Figure 7:
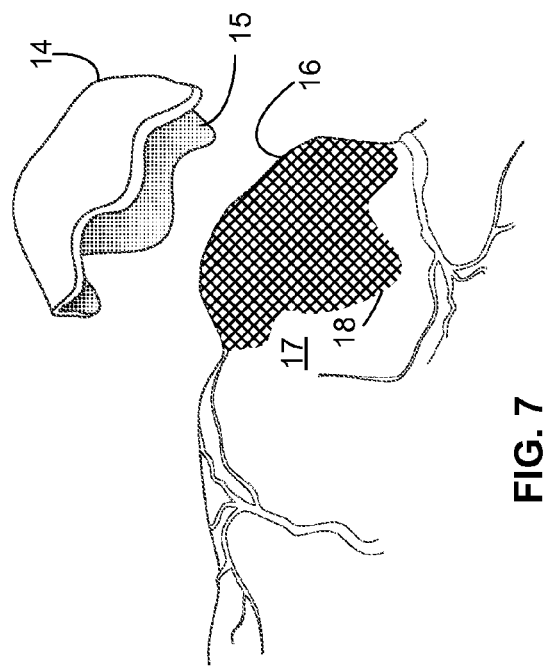
FIG. 7 is a schematic view of a glass, radiation-source having a three dimensional surface geometry and an irregular shape substantially corresponding to that of a treatment area, according to an embodiment.

FIG. 7 depicts a customized glass, radiation-source 14 for an irregular, three-dimensional treatment area 16. As shown, customized, glass radiation-source 14 has a corresponding sloping surface geometry 15 to facilitate placement in maximum proximity to treatment area 16 and a substantially matching shape to facilitate alignment with contoured or protruding treatment areas 18 and to minimize radiation of healthy tissue 17, according to an embodiment.

Figure 8:
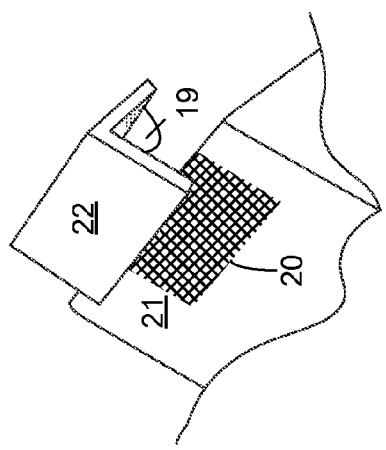
FIG. 8 is a schematic view of a glass, radiation-source having an angular surface geometry substantially corresponding to that of a treatment area, according to an embodiment.

FIG. 8 depicts customized glass, radiation-source 22 having an angular surface geometry 19 so as to facilitate placement in maximum proximity to treatment area 20 and also a substantially matching shape to facilitate alignment with or fit with the boundaries of the treatment area 20 while minimizing radiation to non-treatment area 21, as noted above.

Figure 9:
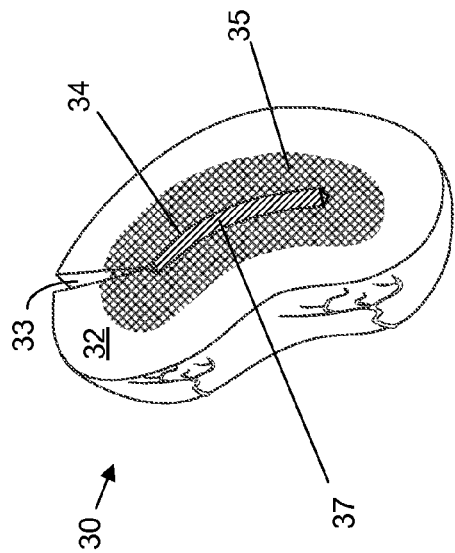
FIG. 9 is a schematic cut-away view of a glass radiation-source embedded in diseased tissue for which the source size and geometries are customized, according to an embodiment.

FIG. 9 depicts a cross-section of a customized glass, radiation-source 37 embedded in diseased organ 30. The size, shape and surface geometry glass, radiation-source 37 is defined by a treatment volume 35, according to an embodiment.

As shown, organ 30 includes non-diseased tissue 35 and substantially crescent-shaped, diseased tissue defining treatment volume 35. The size and shape of treatment volume 35 defines in turn the above-noted parameters of the glass, radiation-source 37 so that when inserted through incision 33 into treatment volume 35, a therapeutic dose of radiation permeates to a generally predictable depth through interfacing treatment area 34 into treatment zone 35 thereby minimizing radiation into non-treatment volume 32 of organ 30.

Figure 11:
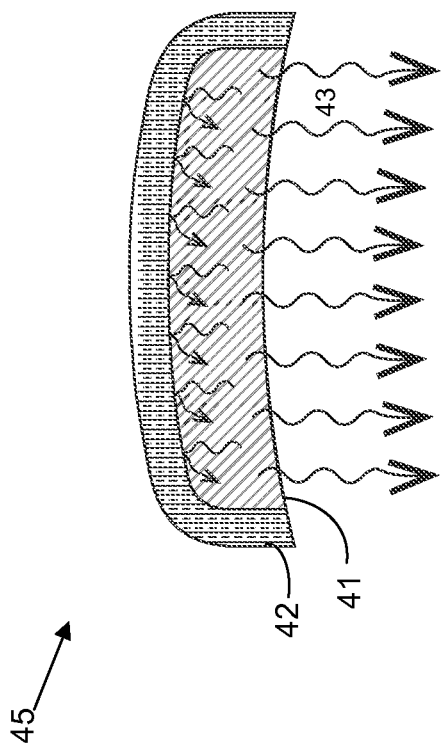
FIGS. 10 and 11 are schematic views of embodiments of a customized, glass-radiation-source having both a radioisotope layer and a shielding layer for shielding and directing radiation, according to embodiments.
Figure 10:
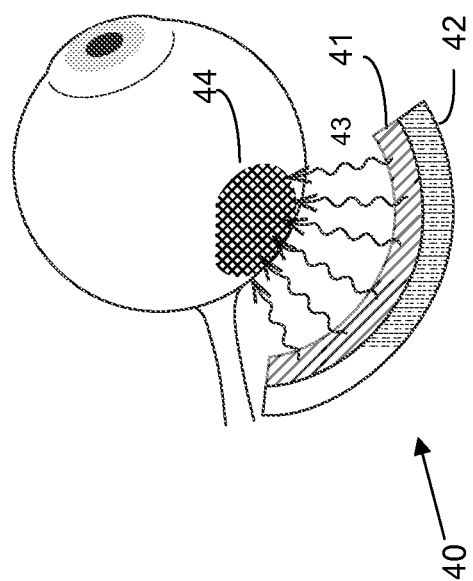

FIGS. 10 and 11 depict composite glass, radiation-sources 40 and 45, respectively; each having both a radioisotope layer 41 and a shielding material layer 42, according to embodiments.

As shown in FIG. 10, the general concavity of source 40 directs radiation 43 towards treatment area 44 while shielding material 42 simultaneously contains or reduces outwardly radiating radiation. Suitable shielding materials include heavy metals like, inter alia, gold, platinum, steel, tungsten, lead or non-metallic materials like polymeric materials or fluids; the particular material chosen in accordance with the radiation type being shielded.

As shown in FIG. 11 shielding layer 42 is configured to reflect or focus radiation 43 in the direction the source geometry directs radiation so as to efficiently utilize available radiation capacity of source 45, according to an embodiment. It should be appreciated that in many embodiments composite, glass-radiation-sources, the shielding material inherently shields and reflects simultaneously. Construction methods described above may also be employed to construct composite glass, radiation-sources.

Figure 12:
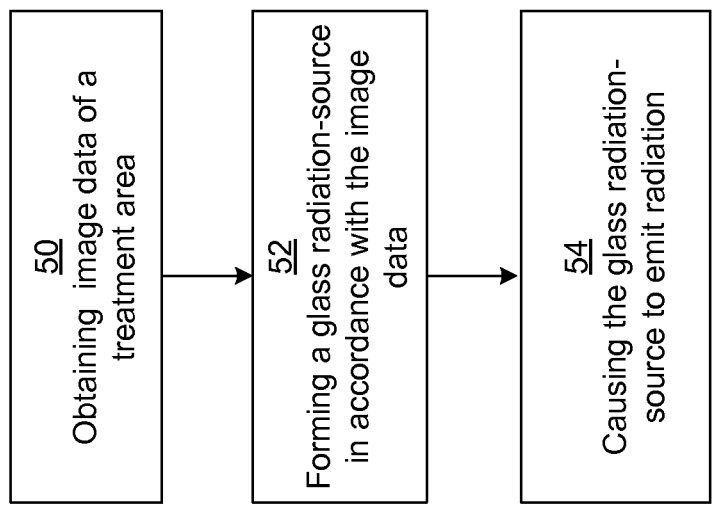
FIG. 12 is a flow chart depicting a method for producing a customized glass radiation source, according to an embodiment.

FIG. 12 is a flow chart depicting a method for producing a customized glass radiation source, according to an embodiment. Specifically, in step 50 image data of the treatment area is captured. The image data includes data that can be used for generating a glass-radiation source having substantially the same shape and surface geometry and size of the treatment area. In step 52, a glass-radiation source is formed in accordance to the image data using the above-described production techniques. In step 54 the glass radiation-source is activated using the above described techniques. It should be noted that step 54 does not have to be implemented as a last step.

It should be appreciated that various combinations of the above-noted features are also included within the scope of the present invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of manufacturing a radiation-source comprising:
   obtaining image data of a treatment area, the image data including surface geometry and shape data;
   forming a glass radiation-source, constructed from neutron-activated glass, in accordance with the image data; and
   causing the glass radiation-source to emit radiation.

2. The method of claim of claim 1, wherein the glass radiation-source has a shape substantially matching at least a portion the shape of the treatment areas so as to minimize radiation in non-treatment area.

3. The method of claim 1, wherein the radiation is selected from the group consisting of alpha particles, beta minus and beta plus particles, Auger electrons, gamma-rays, and x-rays.

4. The method of claim 1, wherein the glass radiation-source is constructed from neutron-activated glass selected from the group consisting of yttrium aluminosilicate, magnesium aluminosilicateholmium-166, erbium-169, dysprosium-165, rhenium-186, rhenium-188, and yttrium-90.

5. The method of claim 1, wherein the glass radiation-source is implemented as a radioisotope encased in an encasement constructed from a material selected from the group consisting of glass forming material, metallic material, and polymeric material.

6. The method of claim 1, wherein the radioisotope is selected from the group consisting of $^{89}$Sr, $^{90}$Sr, $^{169}$Yb, $^{32}$P, $^{33}$P, $^{90}$Y, $^{192}$Ir, $^{25}$I, $^{131}$I, $^{103}$Pd, $^{177}$Lu, $^{149}$Pm, $^{140}$La, $^{153}$Sm, $^{186}$Re, $^{166}$Ho, $^{166}$Dy, $^{137}$C, $^{57}$Co, $^{169}$Er, $^{165}$Dy, $^{97}$Ru, $^{193m}$Pt, $^{195m}$Pt, $^{105}$Rh, $^{68}$Ni, $^{67}$Cu, $^{64}$Cu, $^{109}$Cd, $^{111}$Ag, $^{198}$Au, $^{199}$Au, $^{201}$Tl, $^{175}$Yb, $^{47}$Sc, $^{159}$Gd, $^{212}$Bi, and $^{77}$As.

7. The method of claim 6, wherein the radioisotope is implemented as a particulate radioisotope.

8. The method of claim 7, wherein the radioisotope includes neutron-activated glass.

9. The method of claim 8, wherein the neutron-activated glass is selected from the group consisting of aluminosilicate, magnesium aluminosilicate, and potassium aluminogermanate containing samarium-153, holmium-166, erbium-169, dysprosium-165, rhenium-186, rhenium-188, and yttrium-90.

10. The method of claim 1, further comprising a step of adding a radiation shielding layer from a shield material so as to form an at least partially shielded glass, radiation-source.

11. A composite radiation-source comprising:
    a glass radiation-source, constructed from neutron-activated glass; and
    a shielding material connected to at least part of the glass radiation-source.

12. The composite radiation-source of claim 11, wherein the glass radiation-source is constructed from neutron-activated glass selected from the group consisting of yttrium aluminosilicate, magnesium alumino silicateholmium-166, erbium-169, dysprosium-165, rhenium-186, rhenium-188, and yttrium-90.

13. The composite radiation-source of claim 11, wherein the glass radiation-source is implemented as a radioisotope encased in an encasement, the encasement constructed from a material selected from the group consisting of glass forming material, metallic material, and polymeric material.

14. The composite radiation-source of claim 13, wherein the radioisotope is selected from the group consisting of $^{89}$Sr, $^{90}$Sr, $^{169}$Yb, $^{32}$P, $^{33}$P, $^{90}$Y, $^{192}$Ir, $^{25}$I, $^{131}$I, $^{103}$Pd, $^{177}$Lu, $^{149}$Pm, $^{140}$La, $^{154}$S, $^{186}$Re, $^{188}$Re, $^{166}$Ho, $^{166}$Dy, $^{137}$Cs, $^{57}$Co, $^{169}$Er, $^{165}$Dy, $^{97}$Ru, $^{193m}$Pt, $^{195m}$Pt, $^{105}$Rh, $^{68}$Ni, $^{67}$Cu, $^{64}$Cu, $^{109}$Cd, $^{111}$Ag, $^{198}$Au, $^{199}$Au, $^{201}$Tl, $^{175}$Yb, $^{47}$Sc, $^{159}$Gd, $^{212}$Bi, and $^{77}$As.

15. The composite radiation-source of claim 14, wherein the radioisotope is implemented as a particulate radioisotope.

16. The composite radiation-source of claim 15, wherein the particulate radioisotope includes neutron-activated glass.

17. The composite radiation-source of claim 16, wherein the neutron-activated glass is selected from the group consisting of aluminosilicate, magnesium aluminosilicate, and potassium aluminogermanate containing samarium-153, holmium-166, erbium-169, dysprosium-165, rhenium-186, rhenium-188, and yttrium-90.

* * * * *